(12) United States Patent
Boodaghians et al.

(10) Patent No.: US 9,907,870 B2
(45) Date of Patent: Mar. 6, 2018

(54) SYSTEMS AND METHODS FOR TREATMENT OF CABIN SURFACES AND AIR

(71) Applicant: MAG Aerospace Industries, LLC, Carson, CA (US)

(72) Inventors: Razmik B. Boodaghians, Glendale, CA (US); Shane Nazari, Glendale, CA (US); Christina Ortolan, Long Beach, CA (US)

(73) Assignee: MAG Aerospace Industries, LLC, Carson, CA (US)

( * ) Notice: Subject to any disclaimer, the term of this patent is extended or adjusted under 35 U.S.C. 154(b) by 0 days.

(21) Appl. No.: 15/333,607

(22) Filed: Oct. 25, 2016

(65) Prior Publication Data
US 2017/0035920 A1 Feb. 9, 2017

Related U.S. Application Data

(63) Continuation-in-part of application No. 14/865,685, filed on Sep. 25, 2015, now Pat. No. 9,550,006.

(60) Provisional application No. 62/055,802, filed on Sep. 26, 2014.

(51) Int. Cl.
*A61L 2/10* (2006.01)
*A61L 9/20* (2006.01)
*B64D 11/00* (2006.01)
*A61L 2/24* (2006.01)

(52) U.S. Cl.
CPC ............................ *A61L 2/10* (2013.01); *A61L 9/20* (2013.01); *B64D 11/00* (2013.01); *A61L 2/24* (2013.01); *A61L 2202/25* (2013.01)

(58) Field of Classification Search
CPC .......... A61L 2202/25; A61L 2/10; A61L 2/24; A61L 9/20; B64D 11/00
See application file for complete search history.

(56) References Cited

U.S. PATENT DOCUMENTS

| | | | |
|---|---|---|---|
| 5,222,801 A * | 6/1993 | Neer | B64D 11/00 362/148 |
| 6,470,512 B1 * | 10/2002 | Lau | A47K 3/30 4/612 |
| 8,097,861 B2 * | 1/2012 | Leben | A61L 2/10 250/365 |

(Continued)

FOREIGN PATENT DOCUMENTS

| | | |
|---|---|---|
| DE | 102012006972 A1 | 10/2013 |
| EP | 2492195 A1 | 8/2012 |

(Continued)

OTHER PUBLICATIONS

U.S. Appl. No. 14/865,685, "Final Office Action", dated Jul. 29, 2016, 16 pages.

(Continued)

*Primary Examiner* — Wyatt Stoffa
(74) *Attorney, Agent, or Firm* — Kilpatrick Townsend & Stockton LLP; Dean W. Russell; Kristin M. Crall (57) ABSTRACT

Embodiments relate generally to systems and methods for treating passenger transportation vehicle cabin surfaces and surrounding air. The methods may use organic LEDs to produce ultraviolet light. Systems may be provided to ensure safety and operation of the air treatment only when passengers and personnel are not present in the cabin.

11 Claims, 5 Drawing Sheets

(56) References Cited

U.S. PATENT DOCUMENTS

| | | | |
|---|---|---|---|
| 8,226,887 B2* | 7/2012 | Harmon | A61L 2/10 250/455.11 |
| 9,550,006 B2* | 1/2017 | Boodaghians | A61L 2/10 |
| 2004/0021425 A1* | 2/2004 | Foust | G09F 9/33 315/169.3 |
| 2007/0053188 A1* | 3/2007 | New | A61L 9/20 362/276 |
| 2008/0127411 A1* | 6/2008 | Hoffjann | B60R 15/02 4/664 |
| 2008/0286145 A1* | 11/2008 | Ratcliffe | A61L 2/10 422/24 |
| 2009/0191100 A1* | 7/2009 | Deal | A61L 2/10 422/105 |
| 2010/0032589 A1* | 2/2010 | Leben | A61L 2/10 250/504 R |
| 2010/0187443 A1* | 7/2010 | Leben | A61L 2/10 250/492.1 |
| 2012/0187313 A1* | 7/2012 | Clark | A61L 2/10 250/492.1 |
| 2012/0221192 A1* | 8/2012 | Seibt | B64D 11/02 701/29.1 |
| 2012/0230867 A1* | 9/2012 | Kerr | A61L 2/10 422/24 |
| 2013/0175460 A1* | 7/2013 | Farren | A61L 2/10 250/504 R |
| 2013/0234041 A1* | 9/2013 | Deal | A61L 2/10 250/455.11 |
| 2013/0334438 A1* | 12/2013 | Traubenberg | C02F 1/325 250/435 |
| 2013/0341533 A1* | 12/2013 | Leben | A61L 2/10 250/492.1 |
| 2014/0017135 A1 | 1/2014 | Boodaghians et al. | |
| 2014/0034912 A1* | 2/2014 | Liu | H01L 51/5036 257/40 |
| 2014/0059796 A1* | 3/2014 | Boodaghians | A61L 2/10 15/339 |
| 2014/0241941 A1* | 8/2014 | Kreitenberg | A61L 2/10 422/24 |
| 2014/0271352 A1* | 9/2014 | Stewart | A61L 2/10 422/24 |
| 2016/0089459 A1 | 3/2016 | Boodaghians et al. | |
| 2016/0317690 A1* | 11/2016 | Dayton | A61L 2/26 |

FOREIGN PATENT DOCUMENTS

| | | |
|---|---|---|
| EP | 2772272 A1 | 9/2014 |
| WO | 2016049447 A1 | 3/2016 |

OTHER PUBLICATIONS

U.S. Appl. No. 14/865,685, "Non-Final Office Action", dated Apr. 5, 2016, 16 pages.

U.S. Appl. No. 14/865,685, "Notice of Allowance", dated Sep. 16, 2016, 11 pages.

PCT/US2015/052208, "International Search Report and Written Opinion", dated Nov. 17, 2015, 9 pages.

* cited by examiner

SYSTEMS AND METHODS FOR TREATMENT OF CABIN SURFACES AND AIR

CROSS REFERENCE TO RELATED APPLICATIONS

This application in a continuation-in-part of U.S. Ser. No. 14/865,685, titled "Systems and Methods for Treatment of Cabin Surfaces and Air" filed Sep. 25, 2015, which application claims the benefit of U.S. Provisional Application Ser. No. 62/055,802, filed Sep. 26, 2014, titled "System and Methods for Treatment of Cabin Surfaces and Air," the entire contents of each of which are hereby incorporated by reference.

FIELD OF THE DISCLOSURE

Embodiments of the present disclosure relate generally to systems and methods for treating passenger transportation vehicle cabin surfaces and surrounding air. The methods may use organic LEDs to produce ultraviolet light. Systems may be provided to ensure safety and operation of the air treatment only when passengers and personnel are not present in the cabin.

BACKGROUND

Aircraft and other passenger transportation vehicle facilities can transport infections, viruses, and bacteria across large distances. This transport can happen very rapidly, due to the very nature of travel. Passengers often travel when knowingly sick, and their coughing, breathing, and/or touching surfaces can spread germs to other passengers. Passengers also travel when, often unknowingly, they have been exposed to a virus or other airborne illness that can be spread rapidly.

Aircraft and other passenger transportation vehicles may often be cleaned between routes. This cleaning may simply be trash removal and straightening of the visual area. It is not often the case that the cleaning involves a thorough disinfection of the passenger cabin. Accordingly, many passenger transportation vehicle cabins have air and surfaces that may be contaminated with bacteria, viruses, mold, and/or other airborne illnesses. It is generally desirable for any cleaning systems to be safe and effective. Improved systems and methods for cleaning cabin surfaces and air are described herein.

BRIEF SUMMARY

Embodiments of the invention described herein thus provide systems and methods for treating and disinfecting passenger transportation vehicle cabin surfaces and surrounding air. The methods may use UV lights or organic LEDs (OLEDs) to produce ultraviolet light. The light may kill or otherwise disrupt bacteria, viruses, or airborne-based illnesses. Systems may be provided to ensure safety and operation of the air treatment only when passengers and personnel are not present in the cabin.

One proposed solution provided by the current assignee is described in U.S. Publication No. 2014/0017135 titled "Systems and methods for disinfecting air on board a passenger transport vehicle," the contents of which are incorporated herein by reference.

In one example, there is provided a cabin disinfection system, comprising: one or more disinfection lights positioned on a panel that rotates, a first side of the panel comprising the one or more disinfection lights and a second side of the panel comprising one or more reading or other purpose lights, wherein the first side of the panel is configured to be rotated to face a surface for disinfection. The system may also include a safety system for activating the one or more disinfection lights only when the cabin is empty of passengers and personnel. For example, the safety system may be an external panel that may only activate the cabin disinfection system when a cabin door is closed. The safety system may automatically turn the disinfection system off if the cabin door is opened. The safety system may include a time-delay auto shutoff function.

In a specific example, the one or more disinfection lights comprise ultra-violet organic light emitting diodes (UV OLEDS). They may be flexible organic LEDs.

The system can be mounted on an aircraft wall with one or more connection features for securing the panel with respect to the aircraft wall. The one or more connection features may be a vibration dampening feature, a light socket connection, or a combination thereof.

Embodiments also relate to the system installed on-board a passenger aircraft. There may also be provided a method for disinfecting an aircraft cabin, comprising:
providing a rotating panel with one or more UV OLED disinfection lights positioned in the aircraft cabin; and
activating the one or more UV OLED lights only when the cabin is empty of passengers and personnel.

DETAILED DESCRIPTION

Embodiments of the present invention provide systems and methods for treating passenger transportation vehicle cabin surfaces and surrounding air. Specific embodiments may find particular use on-board an aircraft, and specifically in an aircraft cabin. Although cabin treatment for aircraft surfaces and air is described throughout the remainder of this document, it should be understood that the systems and methods described herein may be used on any passenger transportation vehicle or in any other environment that houses a large number of people and is desirably rapidly cleaned. It should also be understood that the systems described may be found to clean only surfaces, only air, or a combination thereof. The surfaces that may be optionally disinfected include but are not limited to hard surfaces, grooved surfaces, plastic, fabric, carpet, or any other type of surface present in a passenger cabin.

Figure 1:
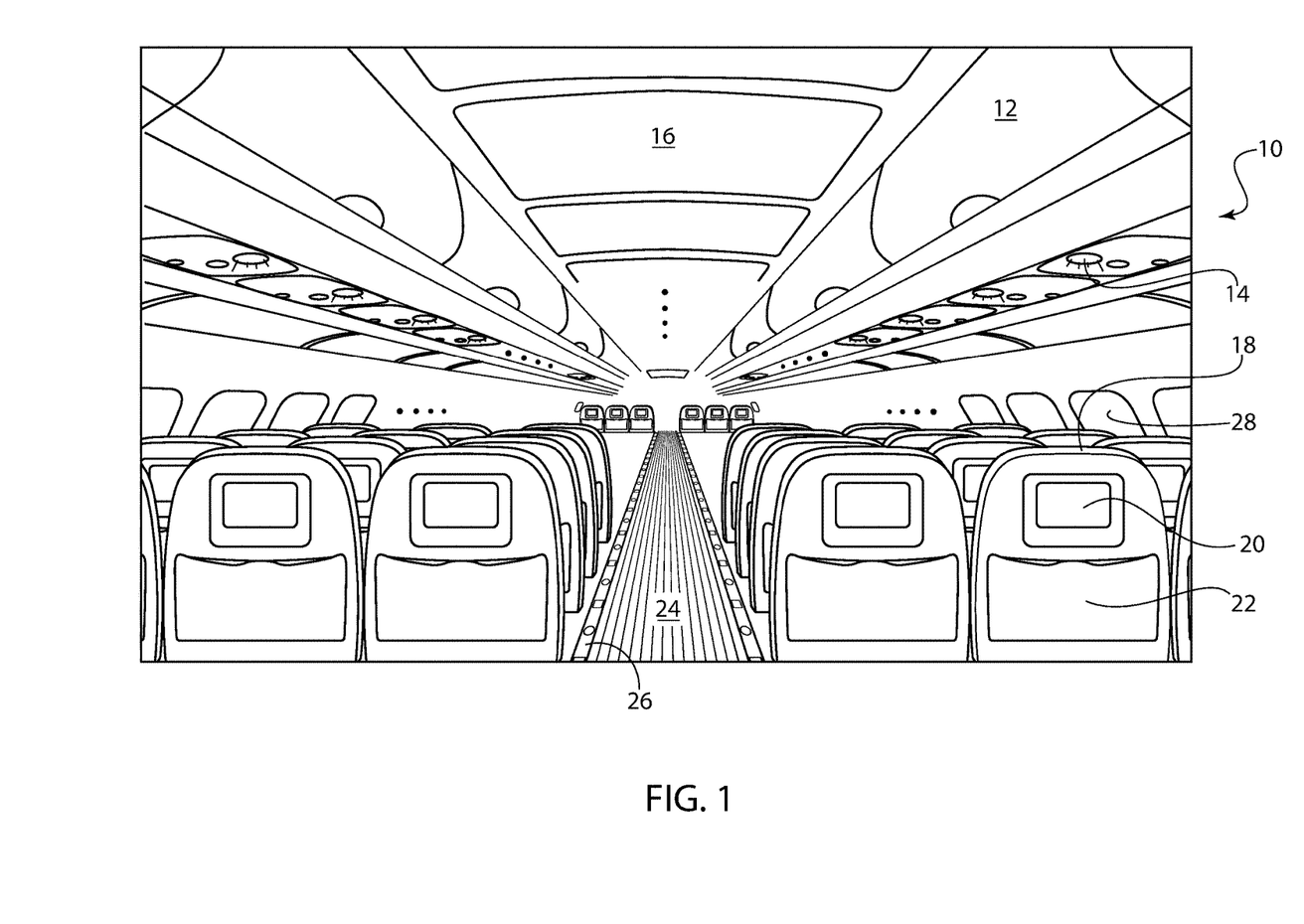
FIG. 1 shows a perspective view of a cabin interior with various locations where disinfection lights may be located.

As shown in FIG. 1, one embodiment described herein may be used on an aircraft passenger cabin 10. The cabin 10 will generally have overhead compartments 12, overhead lighting 14, ceiling panels 16, seats 18, in-flight entertainment (IFE) units 20, seat back trays 22, a floor surface 24, floor lighting 26, and windows with window covers 28. Cabins may also be provided with user interfaces at the seat level or remote controls for operating the IFE units. Cabins may also be provided with curtains dividing the economy cabin from the first class and/or business class cabin. Cabins may also be provided with monuments or storage areas for storing larger passenger items, such as foldable wheelchairs, or for hanging items, such as passenger jackets. Cabins may also be provided with one or more galleys for food and drink preparation and storage. Cabins may also be provided with one or more lavatories housing a toilet, a countertop, and a sink basin. Any or all of these cabin surfaces or areas are candidates for the disinfection systems and methods described herein.

Figure 2:
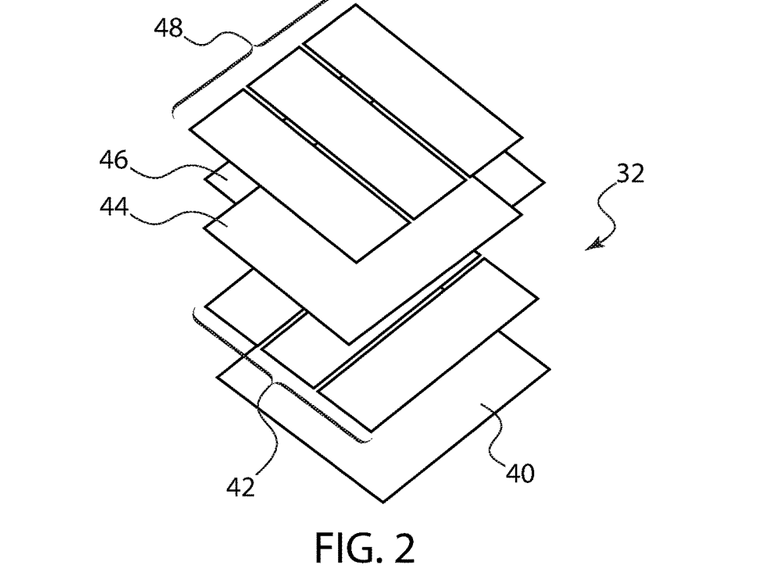
FIG. 2 shows a schematic perspective view of one embodiment of an organic LED that may be used in accordance with embodiments described herein.

In one embodiment, the systems described may use ultraviolet (UV) light for disinfection. In a specific embodiment, the UV light used may be an organic LED (OLED). A specific example may include an OLED light that produces UV-C light. One exemplary OLED is illustrated by FIG. 2. Exemplary OLEDs may be manufactured and produced by a number of companies, and they may have any number of properties. The general goal is that the UV light or the OLED selected may operate within a wavelength that will disinfect the desired surfaces and/or the surrounding air. Exemplary wavelengths include but are not limited to approximately 240 to 285 nm. A single wavelength may be used throughout the disinfecting treatment process. In another example, it is possible to use varying wavelengths throughout the disinfecting treatment process in order to target various types of microorganisms, such as viruses, bacteria, and protozoans.

In other examples, the wavelength used may be tunable between wavelengths. For example, in any of the embodiments described herein, it is possible for the disinfection light(s) to operate within a variety of treatment wavelengths. At disinfection wavelengths, the light may function to disinfect between 240 nm to about 285 nm in wavelength. In this example, a single light may be tunable between various wavelengths. A controller may be provided that will control the wavelength emitted by the light. In another example, it may be possible to provide a cluster of disinfection lights that are tunable. For example, a first light (or set of lights) may be tunable to a first wavelength. A second light (or set of lights) may be tunable to a second wavelength. Both the first and second lights (or sets of lights) may be positioned on one surface, such that the one surface can emit varying wavelengths of light. Although two sets or clusters of lights are described, it is possible that there may be more than two clusters or sets of lights. For instance, there may be 3-5 LEDs at different wavelengths so that varying wavelengths could be selected/alternated based on usage or needs.

In use, the disinfection lights may be activated when the cabin 10 is empty of passengers or personnel. The disinfection lights may function to disinfect the cabin surfaces and cabin air. The disinfection lights are generally activated and allowed to treat the cabin surfaces and cabin air for a specified period of time. The disinfection sequence may take anywhere from about a few seconds to a few minutes, based on the system design.

The disinfection lights may generally be operated via a safety system. If a human eye is exposed to UV light, damage may occur, so the safety system may be configured to only allow the disinfection sequence to take place only when certain requirements are met. For example, it may be possible for the lights to be activated only when the passenger door is closed and/or only from an external service panel. This may prevent inadvertent activation when someone is on-board the aircraft. The service panel may have an optional indicator that indicates whether or not the disinfection lights are currently activated. In another example, it may be possible for the lights to be activated only by an external key to start the lights. In another example, it may be possible for the lights to be activated only when all aircraft systems are powered down. In another example, it may be possible for the lights to be activated only when the aircraft is parked. In another example, it may be possible for the lights to be activated only after a certain amount of time has elapsed since aircraft shut down and/or aircraft passenger door closing. In another example, it may be possible for the lights to be activated by a particular pre-programmed sequence. One exemplary sequence could be that once the aircraft is parked and the aircraft engines are off, certain checks may be made, and then the system may be activated only once the passenger door is closed and locked, using the auxiliary power unit to run the sequence. Combinations of the above safety features are also possible and considered within the scope of this disclosure.

In another example, the lights may have an automatic shut-off feature. The automatic shut-off feature may be time-based, such that after a certain number of minutes, the lights are automatically powered down. There may be provided a time delay before the lights may be turned back on again. In another example, if the lights are currently turned on, they may be automatically shut off upon unlocking and/or opening of the passenger door. In one example, it is possible for the automatic shut-off feature to have a built in redundancy. There may be provided circuits such that if the lights do not shut off during closure of a first circuit, they will shut off during closure of a second circuit.

One benefit if the UV light selected is an OLED is that OLEDs may be provided in any desired shape. For example, they may be installed on a flat or a curved surface. OLEDs may be flexible such that they can be manipulated to fit or conform to a curved surface. The OLEDs can be made in long continuous shapes where power connections may only be needed at one end. FIG. 2 illustrates one embodiment of a potential OLED light 32 that may be used in accordance with various embodiments described. It shows a substrate 40, an anode 42, a conductive layer 44 (which may be organic molecules or polymers), an emissive layer 46 (which may be organic molecules or polymers), and a cathode 48. Although not shown, there may also be provided an optional cover for the light 32. The optional cover may be particularly useful in instances in which the light 32 is positioned in a high traffic, heavy use area.

In one embodiment, one or more OLED disinfection lights may be installed along or with respect to one or more surfaces of the cabin 10. Exemplary locations are described in more detail below. In another embodiment, one or more UV OLED disinfection lights, may be installed on a temporary structure that may be moved into the cabin 10 by maintenance crew and then removed after the disinfection process has taken place. For example, it may be possible to provide roll-out OLED mats and/or carts. Such temporary structures may use aircraft power. Such temporary structures may be configured to be activated from outside the aircraft, such as via a service panel. Such temporary structures may be configured to be activated remotely.

Figure 3:
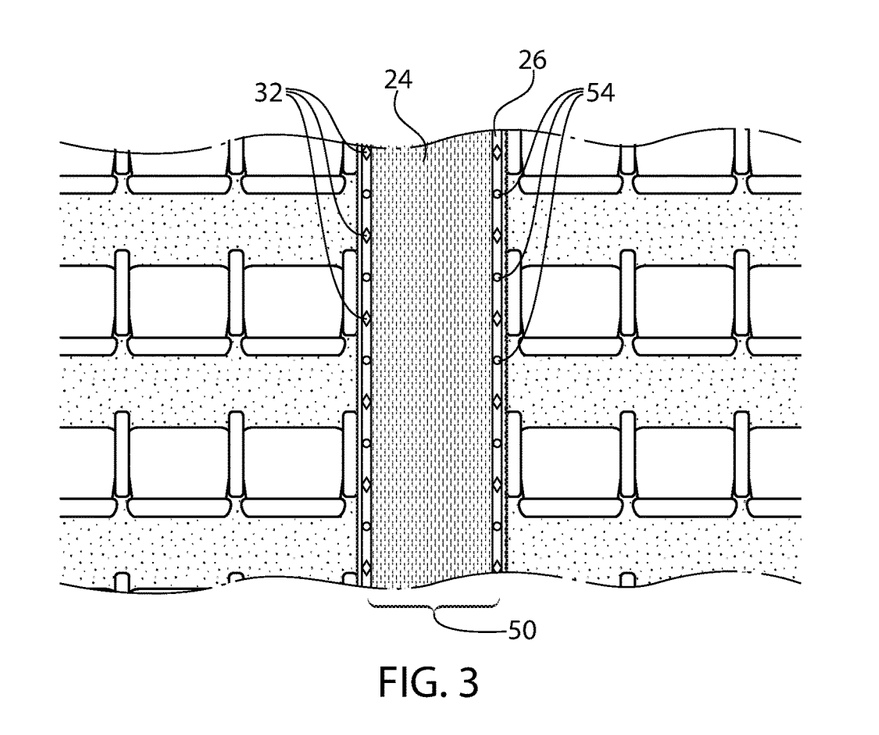
FIG. 3 shows a top perspective view of a floor lighting track, having disinfections lights that alternate with respect to emergency lights.

If installed in the cabin 10, the one or more UV OLED disinfection lights 32 may be installed in or along existing light fixtures or tracks. For example, in one embodiment, one or more UV OLED disinfection lights 32 may be installed along the floor surface 24. In a specific example, the one or more UV lights 32 may be installed along the floor lighting track 26 on the aisles. It is possible for the floor lighting track 26 to contain typical emergency lighting, as well as the one or more UV OLED lights 32 in the same track. For example, an emergency light may be alternated with a UV OLED light. This example is illustrated by FIG. 3. In this example, there is shown a floor lighting track 26 positioned alongside both sides of an aircraft aisle 50. Each floor lighting track 26 has a series of disinfection lights 32 and a series of emergency lights 54. In an emergency situation where exit lighting is required, the emergency lights 54 will be activated. In a disinfection situation, the disinfection lights 32 will be activated. It is generally envisioned that the disinfection vs. emergency lighting activations will be situationally-based, based on different inputs.

The emergency lighting system operation is generally designed to function according to emergency protocol and trigger when necessary. It is possible for the emergency lighting system to have a completely separate controlling system in order to ensure no failure of the emergency lighting system occurs. In one example, the structure that houses an emergency light may also house the UV OLED disinfection lights, for example, in an alternating pattern as shown. The function and power source of the emergency lighting would remain unaltered. This would allow the emergency lighting system and the disinfection lighting system to be powered and to function independently from one another. For safety reasons, it is preferred that the floor disinfection light system not be coupled or shared with the emergency lighting power supply course. The disinfection lights 32 and emergency lights 54 are activated via different inputs indicating which set of lights should be activated, depending upon the situation. It is envisioned that only the disinfection crew would have access to the activation system or controller for the disinfection lights. This can ensure that the disinfection lights are activated only when the aircraft is free of human beings or animals or any other creature that could be adversely affected by the UV disinfection lights.

In the figures shown, a single floor lighting track 26 houses or otherwise contains both the disinfection lights 32 as well as the emergency lights 54. The lights are simultaneously positioned along the same track. (As described herein, the disinfection lights may be UV OLED lights, but it should be understood that the use of other disinfection lights is possible and considered within the scope of this disclosure.) The floor lighting track 26 is generally longitudinal with the aircraft longitudinal axis, such that the track borders either side of the aircraft exit aisle 50. The floor lighting track 26 can generally be provided with a track cover that protects the lights from being stepped on or otherwise damaged. In another example, the track 26 may be positioned along an overhead area, such as along the overhead bins, along the aircraft ceiling, or elsewhere, as described in more detail below.

In another example, it is possible for the floor lighting track 26 to house combination lights. The combination lights may have both disinfection lighting (about 240 to about 285 nm in wavelength), as well as emergency lighting. The wavelength of light output will be dependent upon the situation and the input information delivered to the lighting track.

In another embodiment, the one or more UV OLED disinfection lights 32 may be installed along the window or wall area. They may be installed as individual lights or along a channel containing a plurality of lights. In another example, it is possible for one or more UV OLED disinfection lights 32 to be installed along upper channels. For example, the upper channels may be positioned along a location where the overhead compartments are located. For example, channels may be located at one or more joints where the overhead compartments meet the ceiling portion of the fuselage. Channels may be located in the lighting channels by the overhead bins. Channels may be located at the overhead user interface. The channels containing a plurality of lights in any of these embodiments may be similar to the floor lighting track described above. There may be alternating disinfection lights with visible lights. There may be combination lights provided therein. Additionally or alternatively, it is also possible for the UV OLED disinfection lights 32 to be installed as individual lights.

In another embodiment, the one or more UV OLED disinfection lights 32 may be located on or near the location where the overhead compartment lights (and usually an attendant call button) are located, generally above cabin seats. The installation may be retrofit or the light may be positioned with the unit to be initially installed. However, there is generally not a user-activated option for activating the UV OLED light for safety reasons. It is possible to provide a single light per row of seats, it is possible to provide a single light per seat, or any combination thereof.

In another embodiment, the one or more UV OLED disinfection lights 32 may be positioned along or within regular ducting of the aircraft.

Figure 4:
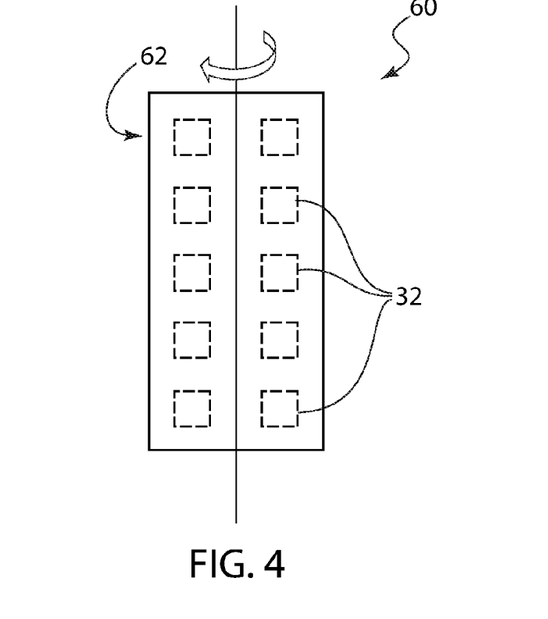
FIG. 4 shows a schematic view of one embodiment of a panel that rotates.
Figure 5:
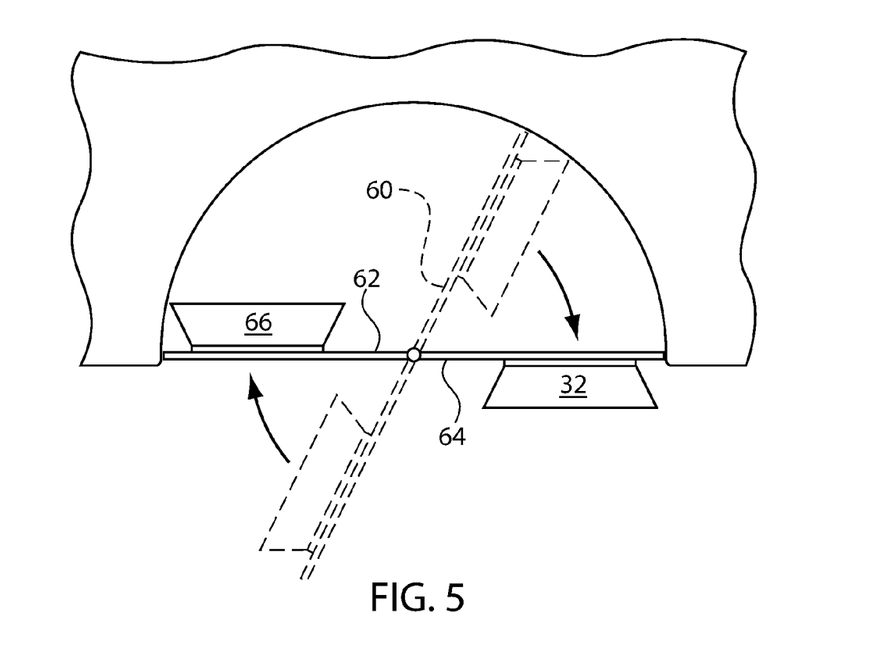
FIG. 5 shows a schematic view of a panel that rotates, having disinfection lights on one side of the panel, and reading or other cabin lights on an opposite side of the panel.
Figure 6:
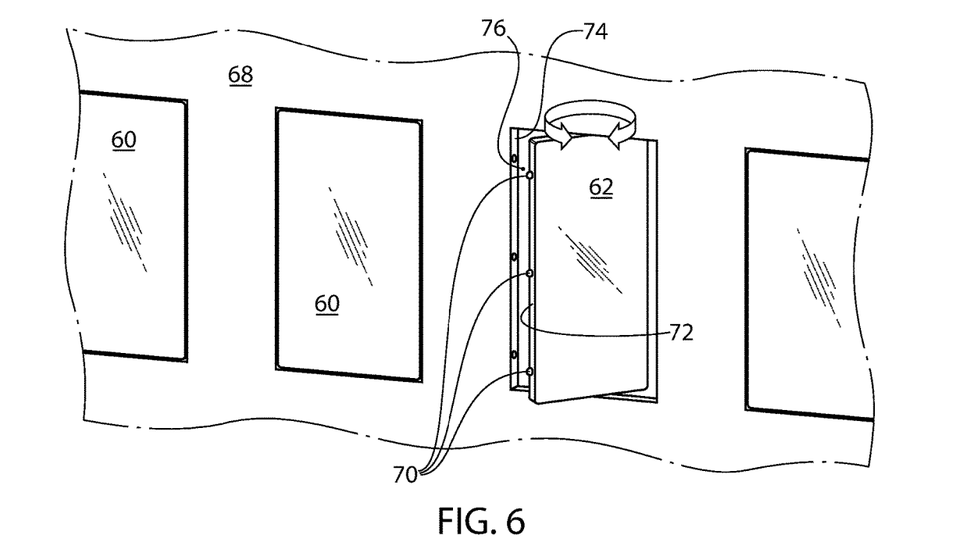
FIG. 6 shows a front perspective view of an aircraft wall having a plurality of panels, with one panel being rotated.

In another embodiment, the UV OLED disinfection lights 32 may be positioned on one or more rotating wall, ceiling, or floor panels, or otherwise provided as having a double-sided installation. In this example, the lights may be provided on panel(s) 60 that are caused to rotate to expose the UV OLED disinfection lights when activated. One example is illustrated by FIGS. 4-6. For example, there may be provided one or more disinfection lights 32 on one side of a wall panel 60 and a typical cabin surface on the other side 62 of the panel. For example, a floor or ceiling panel may have standard materials on one side for in-flight use, and the reverse side would have OLEDs. During normal flight or other non-disinfection times, the cabin surface panel side 62 will face the interior of the cabin. When disinfection is to be conducted, the panel may be activated to rotate to expose the disinfection lights 32 to the cabin, such that the disinfection light side of the panel 60 is facing the interior of the cabin. Disinfection may take place under one or more of the safety precaution activation features described. Upon completion of disinfection, the one or more panels 60 may be caused to rotate back to the cabin surface side 62. This can eliminate the need for a protective layer on the OLED because it will not face passenger or personnel or otherwise be subject to potential tampering or touching.

In the example illustrated by FIG. 5, a panel 60 may be provided that has one or more disinfection lights 32 on a first panel side 64 and one or more reading or other purpose lights 66 on an opposite side (the cabin surface side 62). Although referred to as reading lights 66, it should be understood that the lights 66 may be any type of light that provides illumination in the visible spectrum to the cabin for any purpose. The panel 60 may be a side panel of the aircraft or an overhead panel of the aircraft. In use during flight, the cabin surface side 62 (with the one or more reading lights 66) faces the cabin interior. The panel 60 may include controls for the reading lights 66. Alternatively, the controls for the lights may be positioned on an armrest, a seat back, and overhead panel, or elsewhere for passenger access. When the flight is complete and the cabin is empty of people, the panel 60 may be rotated so that the disinfection lights 32 on the first panel side 64 face the cabin interior. An example of a plurality of panels with one being rotated as illustrated by FIG. 6. The panels 60 may be rotated a complete 180° turn and lock into place along the aircraft wall 68. Alternatively, the panels may be rotated only a portion of the turn, such that in disinfection use, the panels maintain an angle with respect to a longitudinal axis of the aircraft. In this example, the panels may radiate disinfection light at varied angles.

If the panels 60 are designed to lock into place along the aircraft wall 68, one or more connection features 70 may be provided along panel edges 72, along an interior portion 74 of an aircraft wall opening 76, or both. Connection features may function to connect and secure the panel 60 in place with respect to the wall opening 76. Connection features 70 may additionally function to provide power sockets at securement/connection points. Connection features 70 may additionally function to provide shock absorbing features, which are intended to protect the lights 32, 66 in the event of vibration or shock (which may be experienced during any time of the flight, such as during takeoff, flight, and/or landing).

Figure 7:
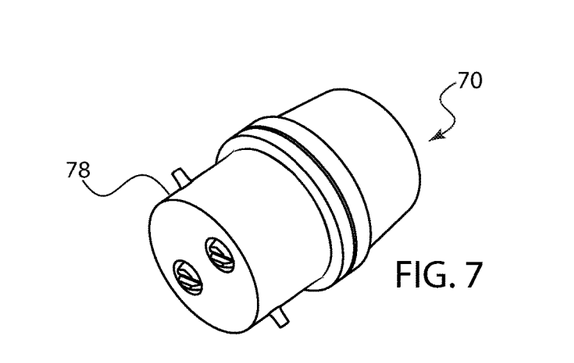
FIG. 7 shows a perspective view of one example of a shock absorbing feature that may be used to secure the panel in place with respect to the aircraft wall.
Figure 8:
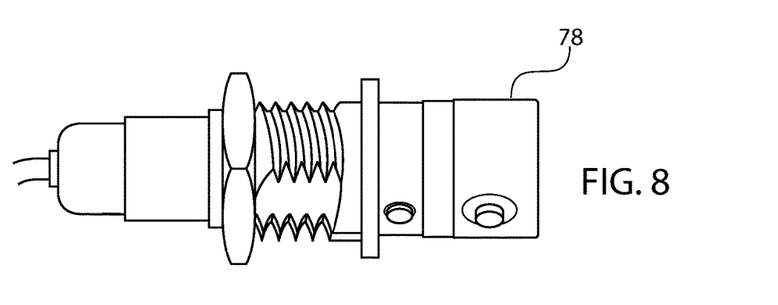
FIG. 8 shows a perspective view of another example of a shock absorbing feature that may be used to secure the panel in place with respect to the aircraft wall.
Figure 9:
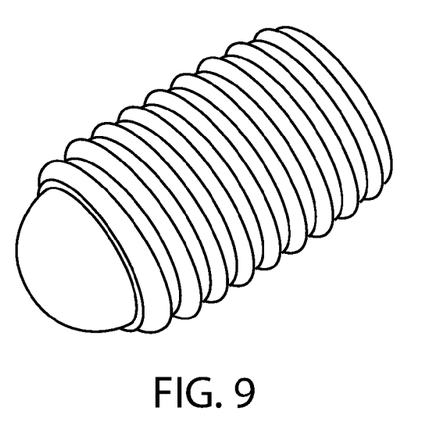
FIG. 9 shows a perspective view of one example of a ball spring plunger that may be used to secure the panel in place with respect to the aircraft wall.

Various types of connection features 70 may be provided on a single panel 60. Exemplary non-limiting connection features 70 are described herein. One specific example of a component that can dampen vibration and/or isolate noise is a Cellasto® polyurethane elastomer manufactured and sold by BASF Corporation, of New Jersey. Examples of components that can provide light bulb power socket connection are illustrated by FIGS. 7 and 8. The components may generally include an electrical connection end 78. The electrical connection end portion will be associated with either the panel edge 72 or the wall opening 76, and a receiving portion will be associated with the other of the panel edge 72 or the wall opening 76. FIG. 9 illustrates a ball spring plunger, which can provide an alternate embodiment that could help dampen vibration and otherwise secure the panel with respect to the aircraft wall.

Once the panel rotation movement is complete, connection features 70 cooperate to maintain the panel in a stationary position. The stationary position will generally be the panel being locked in place and in a flat position against the aircraft wall. The connection features 70 function to provide a socket/housing.

Figure 10:
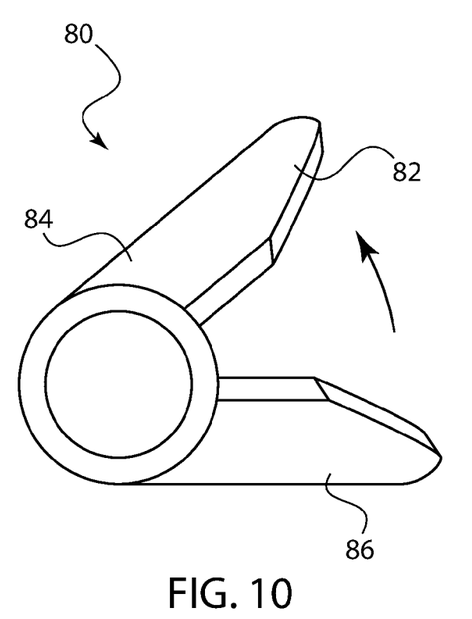
FIG. 10 shows a perspective view of one example of a hinge feature that may be used to offer multiple holding positions and to secure the panel in place with respect to the aircraft wall.

FIG. 10 illustrates an alternate connection feature 80. This connection feature 80 is provided as one or more hinges 82. The hinges 82 can move and secure the panel 60 in varying angular positions with respect to the aircraft wall. One hinge arm 84 will be secured to the wall opening 76 and a second hinge arm 86 will be secured to the panel edge 72. An input system/controller may be programmed to maneuver the hinges such that the panel opens at one of a plurality of desired angle ranges.

In another example, the UV OLED disinfection lights 32 may be positioned behind a sliding cover or panel. This can be to prevent the lights from being accessible or viewable when disinfection is not in process. When disinfection is to be conducted, the sliding cover or panel can be retracted to expose the lights for disinfection. When disinfection is complete, the sliding cover or panel can be moved to cover the lights.

In any of the examples described, it is possible for the disinfection lights to be an OLED flexible light, such that it can be bent to accommodate and/or fit with respect to a curved or non-standard surface. The OLEDs may be provided in strips, sheets, or as single point light sources. There may be a protective layer provided over the light.

The UV OLED disinfection light system may rely on the same power as traditional cabin lighting. In other examples, the light system may rely on alternate sources of power, such as an auxiliary power unit or other options.

Changes and modifications, additions and deletions may be made to the structures and methods recited above and shown in the drawings without departing from the scope or spirit of the disclosure or the following claims.

What is claimed is:

1. A disinfection system mounted on an aircraft having a longitudinal axis, the disinfection system comprising:
   one or more disinfection lights positioned on a panel that rotates, a first side of the panel comprising the one or more disinfection lights and a second side of the panel comprising one or more reading or other purpose lights,
   wherein the panel is configured to be rotated only a portion of a 180° turn, such that when in a disinfection position, the panel maintains an angle with respect to the longitudinal axis of the aircraft and directs the disinfection lights at varied angles or directions.

2. The system of claim 1, further comprising a safety system for activating the one or more disinfection lights only when the aircraft is empty of passengers and personnel.

3. The system of claim 1, wherein the one or more disinfection lights comprises ultra-violet organic light emitting diodes (UV OLEDS).

4. The system of claim 3, wherein the one or more disinfection lights comprise flexible organic UV LEDs.

5. The system of claim 1, wherein the system is mounted on an aircraft wall and further comprising one or more connection features for securing the panel with respect to the aircraft wall.

6. The system of claim 5, wherein the one or more connection features comprise a vibration dampening feature, a light socket connection, or a combination thereof.

7. The system of claim 2, wherein the safety system comprises an external panel that may only activate the disinfection system when a cabin door is closed.

8. The system of claim 2, wherein the safety system automatically turns the disinfection system off if a door of the aircraft is opened.

9. The system of claim 2, wherein the safety system comprises a time-delay auto shutoff function.

10. The system of claim 1, installed on-board a passenger aircraft.

11. A method for disinfecting an aircraft cabin, comprising:
    a rotating panel with one or more UV OLED disinfection lights positioned in the aircraft cabin, a first side of the panel comprising the one or more UV OLED disinfection lights and a second side of the panel comprising one or more reading or other purpose lights;

rotating the panel only a portion of a 180° turn, such that when in a disinfection position, the panel maintains an angle with respect to a longitudinal axis of the aircraft cabin and directs the disinfection lights at varied angles or directions; and
activating the one or more UV OLED lights only when the cabin is empty of passengers and personnel.

* * * * *